(12) United States Patent
Barreca

(10) Patent No.: US 6,869,614 B2
(45) Date of Patent: *Mar. 22, 2005

(54) CHEWING GUM CONTAINING CALCIUM

(76) Inventor: Jack Barreca, 180 Cook St., #210, Denver, CO (US) 80206

( * ) Notice: Subject to any disclaimer, the term of this patent is extended or adjusted under 35 U.S.C. 154(b) by 26 days.

This patent is subject to a terminal disclaimer.

(21) Appl. No.: 10/646,503

(22) Filed: Aug. 21, 2003

(65) Prior Publication Data

US 2004/0037788 A1 Feb. 26, 2004

Related U.S. Application Data

(63) Continuation of application No. 10/316,700, filed on Dec. 10, 2002, now Pat. No. 6,652,839, which is a continuation of application No. 09/664,630, filed on Sep. 19, 2000, now Pat. No. 6,491,540.
(60) Provisional application No. 60/154,972, filed on Sep. 20, 1999.

(51) Int. Cl.[7] .............................. A61K 9/28; A61K 9/68; A61K 47/00; A23G 3/00; A23G 3/30
(52) U.S. Cl. ........................ 424/440; 424/48; 424/439; 424/440; 424/441; 426/3; 426/660
(58) Field of Search .......................... 424/48, 439, 440, 424/441; 426/3, 660

(56) References Cited

U.S. PATENT DOCUMENTS

| | | |
|---|---|---|
| 1,298,670 A | 4/1919 | Cramer |
| 3,894,154 A | 7/1975 | Graff et al. ..................... 426/5 |
| 4,150,161 A | 4/1979 | Rudolph et al. ............... 426/3 |
| 4,156,740 A | 5/1979 | Glass et al. .................... 426/3 |
| 4,157,402 A | 6/1979 | Ogawa et al. .................. 426/5 |
| 4,223,023 A | 9/1980 | Furda .......................... 424/180 |
| 4,250,196 A | 2/1981 | Friello ............................ 426/5 |
| 4,292,329 A | 9/1981 | Ogawa et al. .................. 426/5 |

(List continued on next page.)

FOREIGN PATENT DOCUMENTS

| | | |
|---|---|---|
| DE | 3941490 A1 | 6/1991 |
| FR | 2 540 707 | 2/1983 |
| JP | S59-025646 | 2/1984 |
| WO | WO 9818339 | 5/1998 |
| WO | WO 98/23165 | 6/1998 |
| WO | WO 00/06127 | 2/2000 |

OTHER PUBLICATIONS

Sato et al., "On Drowsiness Preventive Gum that Contains Guarana Extract", 1988, pp. 1–11.
The Sydney Morning Herald, "Smarter up your act," Sep. 11, 1999, 4 pages.
Morton JF. "Widspread tannin intake via stimulants and masticatories, especialy guarana, kola nut, betel vine, and accessories"; Basic Life Sci 1992; 59:739–65.
Miura et al. "Effect of guarana on exercise in normal and epinephrine–induced glycogenolytic mice"; Biol PHarm Bull, Jun. 1998 21(6)646–8.
Sloan, Elizabeth A., "The Ten Top Functional Food Trends", Food Technology, vol. 54, No. 4, Apr. 2000.
Arellano, "More Amore? Herbal Gum Makers Cater to Natural Urges", Detroit Free Press, Mar. 29, 1994.
Horovitz, "Sticky business Ptooie! Gum on the outs with U.S. chewers", USA Today, Jul. 16, 1998.

Primary Examiner—Thurman K. Page
Assistant Examiner—S. Tran
(74) Attorney, Agent, or Firm—Sheridan Ross P.C.

(57) ABSTRACT

A gum, lollipop and lozenge having at least two separate components, with at least one of such components containing amounts of herbal, medicinal and/or mineral elements or combinations thereof.

12 Claims, 2 Drawing Sheets

U.S. PATENT DOCUMENTS

| | | | | |
|---|---|---|---|---|
| 4,316,915 | A | 2/1982 | Friello et al. | 426/5 |
| 4,400,372 | A | 8/1983 | Muhler et al. | 424/48 |
| 4,466,983 | A | 8/1984 | Cifrese et al. | 426/5 |
| 4,496,592 | A | 1/1985 | Kuwahara et al. | 426/5 |
| 4,512,968 | A | 4/1985 | Komiyama et al. | 424/48 |
| 4,513,012 | A | 4/1985 | Carroll et al. | 426/5 |
| 4,642,235 | A | 2/1987 | Reed et al. | 426/5 |
| 4,647,450 | A | 3/1987 | Peters et al. | 424/48 |
| 4,683,138 | A | 7/1987 | Glass et al. | 426/5 |
| 4,738,850 | A | 4/1988 | Thakur et al. | 424/468 |
| 4,792,453 | A | 12/1988 | Reed et al. | 426/5 |
| 4,963,367 | A | 10/1990 | Ecanow | 424/485 |
| 4,971,806 | A | 11/1990 | Cherukuri et al. | 426/5 |
| 4,975,288 | A | 12/1990 | Hager et al. | 428/5 |
| 4,980,178 | A | 12/1990 | Cherukuri et al. | 426/5 |
| 4,997,654 | A | 3/1991 | Corsello et al. | 424/440 |
| 5,077,051 | A | 12/1991 | Gallopo et al. | 424/435 |
| 5,078,460 | A | 1/1992 | Holsinger | 312/244 |
| 5,125,819 | A | 6/1992 | Hager et al. | 425/133.1 |
| 5,248,508 | A | 9/1993 | Reed et al. | 426/5 |
| 5,324,530 | A | 6/1994 | Kehoe et al. | 426/516 |
| 5,344,659 | A | 9/1994 | Kurihara et al. | 426/3 |
| 5,409,905 | A | 4/1995 | Eby, III | 514/23 |
| 5,431,929 | A | 7/1995 | Yatka et al. | 426/3 |
| 5,474,989 | A | 12/1995 | Hashimoto et al. | 514/55 |
| 5,498,429 | A | 3/1996 | Orlandi et al. | 426/5 |
| 5,554,380 | A | 9/1996 | Cuca et al. | 424/441 |
| 5,569,477 | A | 10/1996 | Nesbitt | 426/5 |
| 5,637,313 | A | 6/1997 | Chau et al. | 424/440 |
| 5,670,163 | A | 9/1997 | Cuca et al. | 424/439 |
| 5,736,175 | A | 4/1998 | Cea et al. | 426/6 |
| 5,747,475 | A | 5/1998 | Nordquist et al. | 514/55 |
| 5,798,101 | A | 8/1998 | Haveson | 424/730 |
| 5,824,291 | A | 10/1998 | Howard | 424/48 |
| 5,827,526 | A | 10/1998 | Dohnalek et al. | 424/440 |
| 5,830,883 | A | 11/1998 | Block et al. | 514/55 |
| 5,834,002 | A | 11/1998 | Athanikar | 424/440 |
| 5,846,557 | A | 12/1998 | Eisenstadt et al. | 424/439 |
| 5,846,952 | A | 12/1998 | Vournakis et al. | 514/55 |
| 5,858,391 | A | 1/1999 | Cuca et al. | 424/439 |
| 5,858,423 | A | 1/1999 | Yajima et al. | 426/3 |
| 5,866,179 | A | 2/1999 | Testa | 426/3 |
| 5,880,109 | A | 3/1999 | Nakaura et al. | 514/55 |
| 5,885,630 | A | 3/1999 | Zurawski et al. | 426/5 |
| 5,891,422 | A | 4/1999 | Pan et al. | 424/49 |
| 5,900,230 | A | 5/1999 | Cutler | 424/49 |
| 5,910,308 | A | 6/1999 | D'Jang | 424/195.1 |
| 5,912,030 | A | 6/1999 | Huzinec et al. | 426/3 |
| 5,916,606 | A | 6/1999 | Record et al. | 426/3 |
| 5,922,347 | A | 7/1999 | Hausler et al. | 424/441 |
| 5,945,107 | A | 8/1999 | Hessel et al. | 424/728 |
| 6,139,872 | A | 10/2000 | Walsh | 424/464 |
| 6,165,516 | A | 12/2000 | Gudas et al. | 424/3 |
| 6,224,872 | B1 | 5/2001 | Shibuya et al. | 424/195 |
| 6,242,019 | B1 | 6/2001 | Bell et al. | 426/74 |
| 6,248,378 | B1 | 6/2001 | Ganan-Calvo | 426/89 |
| 6,350,480 | B1 | 2/2002 | Urnezis et al. | 426/5 |
| 6,491,540 | B1 * | 12/2002 | Barreca | 439/440 |
| 6,652,839 | B2 * | 11/2003 | Barreca | 424/48 |
| 2002/0110581 | A1 | 8/2002 | Ream et al. | 424/440 |
| 2002/0127189 | A1 | 9/2002 | Myers et al. | 424/48 |
| 2002/0159956 | A1 | 10/2002 | Ream et al. | 424/48 |
| 2002/0164398 | A1 | 11/2002 | Johnson et al. | 426/3 |
| 2003/0049208 | A1 | 3/2003 | Ream et al. | 424/48 |
| 2003/0138518 | A1 * | 7/2003 | Kiefer et al. | 426/3 |

* cited by examiner

CHEWING GUM CONTAINING CALCIUM

RELATED APPLICATIONS

This is a Continuation application of prior application Ser. No. 10/316,700 filed on Dec. 10, 2002, now U.S. Pat. No. 6,652,839 which is a continuation of application Ser. No. 09/664,630 filed on Sep. 19, 2000 (now U.S. Pat. No. 6,491,540) and U.S. Provisional Patent Application No. 60/154,972 filed on Sep. 20, 1999. The entire disclosure of the prior applications are considered to be part of the disclosure of the accompanying application and are hereby incorporated by reference.

FIELD OF THE INVENTION

The present invention is directed to functional gums, suckers (e.g., lollipops) and lozenges, and more particularly, to a gum and/or sucker and/or lozenge that has at least an exterior and an interior component, having distinct metabolic and functional characteristics that correspond with the ingredients contained therein.

BACKGROUND OF THE INVENTION

Throughout the ages, human beings have attempted to attain and maintain particular body morphologies, and in particular, have attempted to control their weight so as to conform with then-fashionable mores. During the recent past, a preference for less massive morphologies has been in vogue and a populous genetically ill-equipped to conform with such weight characteristics is bombarded with images of svelte figures in both male and female forms.

The desire of individuals to lose weight and specifically, to lose fatty tissue, has become nearly an obsession in the United States and many other countries. Any simple and safe method toward achieving a slim figure is in great demand. Methods for losing weight include hundreds of advised diets, machines and methods for exercise, various psychiatric techniques involving alteration in mental attitudes, and a variety of surgical techniques. Liposuction has created an entirely new surgical cosmetic industry, but carries a small but significant risk and often leaves the patient with an unsightly cosmetic result due to the inflammatory reaction surrounding where the fatty tissue has been removed by a technique which produces a severe tissue reaction.

Obesity is a serious public health hazard, second in importance only to tobacco. Approximately ⅓ of Americans are seriously overweight according to life insurance data. In approximately 12 million Americans, obesity significantly contributes toward the cause and complications of serious disease. Such conditions include heart and lung disease, many types of cancer, diabetes, high blood pressure, and peripheral arterial disease. This is in addition to how obesity becomes a cosmetic problem. Being overly fat limits both length of life and its quality.

A multi-billion dollar industry has developed in an effort to control weight. The many varied and expensive techniques employed speak to the relative ineffectiveness of the many techniques that have been tried to get rid of excess fat.

Obesity has recently been recognized as a public health hazard of epidemic proportions by the World Health Organization. One of three Americans between the ages of 20–74 are obese (Body Mass Index >30 $Kg/m^2$ body surface). This amounts to 58 million people. The number of obese adults has increased dramatically. In 1980 25% of US adults were obese. The equivalent figure was 33% in 1990. In Europe the equivalent figure is about 40%.

Obesity significantly contributes to the dangers of other diseases in approximately half of those who exceed the threshold description of obesity. For example, 19% of the cost of management of heart disease can be ascribed to obesity. Obesity is also recognized as a co-morbid factor for obese patients suffering from degenerative arthritis, peripheral vascular disease, and many forms of pulmonary disease such as emphysema. The expenditure for products, goods, and services in the management of obesity is estimated to be $33 billion per year. This is 3%–4% of total health care expenditure per year and exceeds that expended for AIDS and cancer.

Obesity is such a prevalent, important and distressing problem that its many methods for suggested management are too well known to deserve more than listing. They include diets that exclude fats and high caloric elements, food supplements, appetite suppressants, exercise machines and regimes, biofeedback and other psychotherapeutic techniques, and a variety of operative techniques. Operations include a number of methods for decreasing the capacity the stomach, gastric by-pass operations, methods to shorten the small intestinal absorption surface, excision of the unwanted fat (lipectomy) and techniques of liposuction. Liposuction is performed approximately 51,000 times each year in the US. The maximum amount of fat that can safely be removed is approximately 2 Kg. Being an operative technique for removing fat, in this case by suction, it inevitably excites an inflammatory response at the operative site, which results not only in post operative inflammation but in subsequent uneven and unsightly scarring beneath the skin where the fat has been removed.

Incorporated by reference in its entirety are the following U.S. patents directed generally to chewing gum compositions, methods and apparatus for making chewing gum, and in particular, methods for enabling one of skill in the art to produce soft-centered chewing gums as contemplated by the present invention. The novelty of the present invention, however, should be understood as being distinguished from such prior art references and such incorporation by reference is only provided for enabling support of the numerous ways in which the particular novel product can be manufactured. The U.S. patents incorporated by reference are as follows: U.S. Pat. Nos. 5,922,347; 5,916,606; 5,912, 030; 5,900,230; 5,885,630; 5,866,179; 5,858,423; 5,846, 557; 5,834,002; 5,827,526; 5,824,291; 5,736,175; 4,156, 740; 5,498,429; 4,466,983; 4,157,402; 5,569,477; 5,125, 819; 5,248,508; 4,975,288; 4,792,453; 4,980,178; 4,683, 138; 5,087,460; 4,292,329; 4,642,235; 4,316,915; 4,513, 012; 4,250,196; 5,431,929; and 4,647,450.

Weight control systems and methods have improved over the years. Indeed, the ancient Romans believed that the vomitorium was penance for their uncontrollable feasting and drinking during long celebrations for their various deities. Modern methods of weight control including arduous and sometimes bizarre workout routines and machines are no less peculiar in modern times. Moreover, with the advent of liposuction, stomach stapling, etc., there appears to be no bounds beyond which humans will go to attain desired physical characteristics as such relate to their weight. The effect of such weight norms has created a $60 billion a year market for diet and weight control products. It is estimated that nearly half of all American women, and a quarter of all men, are on a diet at any given time. As is well known, however, most diets, studies have shown, do not work for nine out of ten people who, after suffering through such diets, quickly regain their weight and often exceed their previous body mass. Such an unfortunate volley of feasting and dieting leads not only to physical harm due to increased rates of diabetes, arterial sclerosis, and other physical health problems, but also to an often devastating decreased estimation of a person's self-worth.

There is thus a long felt but unsolved need for an effective, inexpensive and easy way in which to provide health conscious individuals with diet products to assist in achieving desired weight loss.

SUMMARY OF THE INVENTION

In one embodiment, the present invention is directed to a method and product which provides functional components such as, herbal, medicinal and/or vitamin substances for various applications (e.g., weight control substances) to an individual other than through the consumption of pills, suppositories, diet beverages and/or tasteless and low caloric foodstuffs. In one embodiment, the present invention is directed to a particular gum product having at its center a composition different from the surrounding gum and having distinct functional and metabolic characteristics. For example, various metabolism increasing components can be provided in the interior of a gum in a liquid or semi-liquid form while the gum itself can be of a traditional gum composition and/or may incorporate various other desirable metabolic increasing components to supplement and/or coact with components contained in the liquid center of the gum. Indeed, in one particular embodiment of the present invention, time release capsules may be provided suspended in a liquid medium inside a gum enclosure.

The present discussion pertains principally to a diet control gum/lozenge/lollipop, but the present invention is not so limited and includes one or more combinations of ingredients as set forth, for example, in Tables I and II below, which may be useful in numerous and varied applications. For illustration purposes only, however, the following discusses weight loss applications of the present invention. In one embodiment, chewing of the gum-based product releases the interior liquid substance, thus providing a product and a method desirable by weight conscious individuals who do not wish to publicly announce or disclose their dietary desires. In a preferred embodiment, the substance contained within the gum (e.g. the interior liquid substance) would have as a principal characteristic the capability of increasing a user's caloric burn rate (e.g. by increasing a person's metabolism, adjusting/regulating hormonal activity in an individual, providing fiber to increase a person's feelings of satiety).

In a particular embodiment of the present invention, a gum is utilized having liquid interior components surrounded by the dense gum, for example, the interior having a density less than 10% as dense as the exterior gum, more preferably at least about 15% less dense, and more preferably, at least about 35% less dense than the surrounding gum. The interior liquid components can be herbal, organic, natural, chemical and/or hormonal in nature, and may be selected dependent upon their individual and synergistic characteristics, with the objective being to increase a person's metabolism in order to achieve a higher caloric burn rate and/or to decrease the desire for additional food (e.g. generate a feeling of satiety or fullness). It is within the scope of the present invention to incorporate various known diet control substances in either the gum material itself and/or in the liquid interior material encompassed by the gum material. In a preferred embodiment, however, the surrounding gum material is comprised of traditional gum flavors and compositions and the interior liquid and/or semi-liquid (e.g. gel) components of the present invention comprise diet regulating substances.

Yet another embodiment of the present invention relates to a hard candy substance (e.g. primarily comprising a natural sugar and corn syrup base) often referred to as a "sucker" or "lollipop." The interior of the sucker or lollipop, however, contains a less rigid, soft and/or liquid or semi-liquid component. The enclosed material of the lollipop includes metabolic enhancers for weight and caloric control.

In still another embodiment, a lozenge can be manufactured having a denser exterior and a less dense interior, where either the interior or exterior of the lozenge, or both, contain diet controlling substances. Preferably, diet controlling substances are positioned within the interior of such lozenges so as to facilitate the enjoyment by an individual of consuming the lozenge without the possible unpleasant and/or undesirable taste characteristics of various dietary components within the center of the lozenge.

It will be understood that one purpose of certain embodiments of the present invention is to increase metabolic efficiency and to burn calories in an individual. Herbal additives may be incorporated into such products to aid in the body's ability to digest food and/or to block absorption of fat molecules into the system. For example, chitosan compositions can be utilized either in the interior and/or exterior of the gum, lollipop and lozenge embodiments desired above and hereafter. In addition to chitosan, other fiber-like components, vitamins and minerals (e.g., especially calcium compositions to treat osteoporosis) can be incorporated into the present invention to provide desired feelings of satiety or fullness to an individual using such products and/or to treat various vitamin and/or mineral deficiencies.

While the present invention is primarily directed to administering diet control substances to individuals, it should be understood that other medicinal and/or nutritional and/or biological components can be administered to animals in general (companion pets, livestock, etc.) but preferably humans. Indeed, the present inventor believes that the administration of medicinal compounds to young children can be greatly facilitated by use of the present invention given that children are more apt to take medicine in the form of a lollipop, lozenge or gum, particularly if the taste and flavor and textural characteristics of such candy products are preserved and effective amounts of desired components are delivered to such individuals when consuming such products.

DETAILED DESCRIPTION OF THE PREFERRED EMBODIMENT

Figure 1:
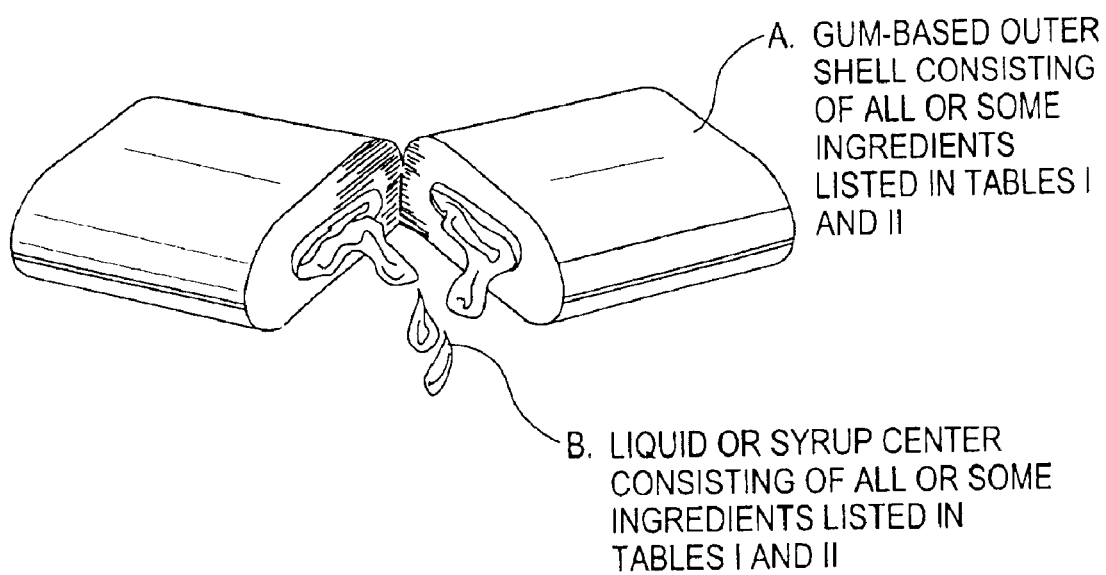
FIG. 1 represents one embodiment of the invention depicting both a gum-based outer shell and a liquid or syrup center, both consisting of all or some ingredients listed in Table I or Table II.
Figure 2:
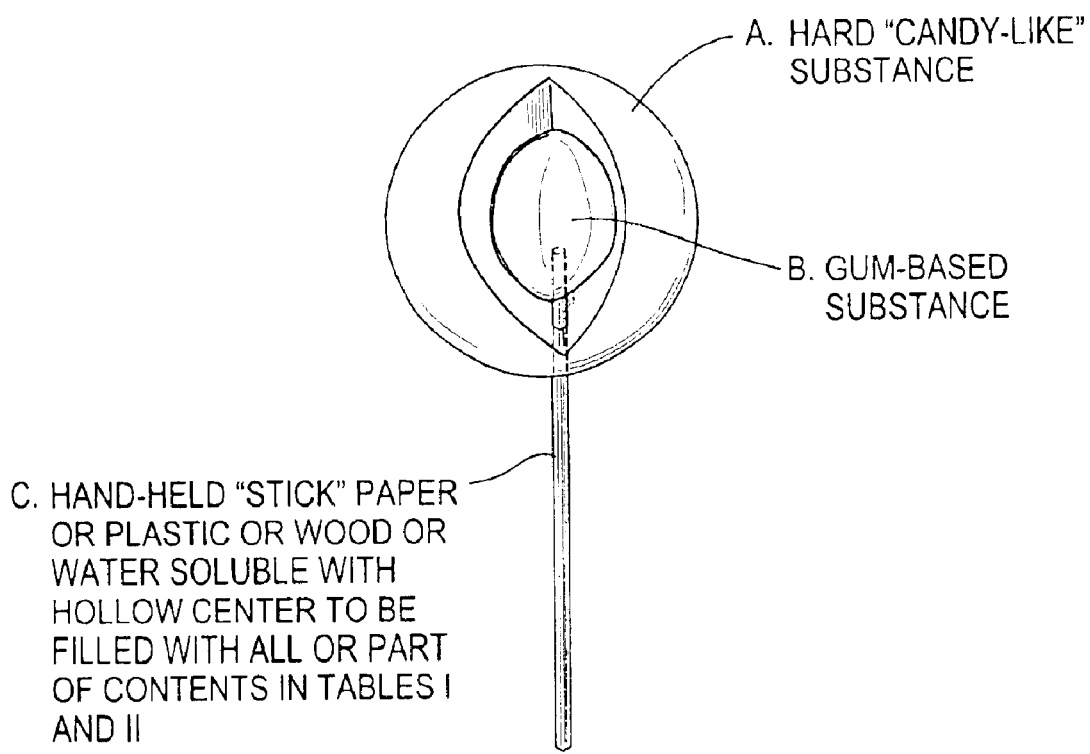
FIG. 2 represents another embodiment of the present invention in a lollipop form.

The following table contains a list of possible components that may be incorporated into the center of the gum, lollipop and lozenge aspects of the present invention:

TABLE I

| | |
|---|---|
| Dexatrim | Diuretics |
| Chitosan | Antacids |
| Oatmeal fiber | Antibiotics |
| Vitamins | Herbal components |
| Mineral supplements | Stimulants |
| Medicinal components | Metabolic enhancers |
| Lipid substances (HDLs) | |
| Chemotherapeutic agents | |

The following U.S. issued patents are also incorporated herein by reference: U.S. Pat. No. 5,474,989 by Hasimoto et al., U.S. Pat. No. 5,747,475 by Norquist et al., U.S. Pat. No. 5,830,883 by Block et al., U.S. Pat. No. 5,880,109 by Nakamura et al., U.S. Pat. No. 4,963,367 by Ecanow, U.S. Pat. No. 4,738,850 by Thakur et al., U.S. Pat. No. 5,846,952 by Vournakis et al., and U.S. Pat. No. 4,223,023 by Furda. It will therefore be appreciated by one of skill in the art that various compositions, formulations, masking agents (e.g., to "mask" unpleasant flavors and/or textures and/or mouth feel characteristics of vitamins, medicinal compounds, minerals, etc.) and binders can be combined with the present structure of the present invention to achieve various desired purposes. For example, controlled release formulations are encompassed by the present invention as are the preparation and use of various different carrier vehicles useful for medicinally administering compositions to animals, time release formulations, compositions having desirable solubility and dissolution rates, and the incorporation into the present invention of food additives such as vitamins, pharmaceutical preparations and other compounds, specifically those that reduce the absorption of lipids such a chitosan.

Both the gum with liquid-type fillers and the sucker with a gum-based center can be comprised of one or more of the following: xanthan, guar, locust bean gum, karaya, gum tragacanth, carrageenans, alginates, gum arabic, corn syrup, sugar, starches, gum bases. While multiple recipes exist, most candy substances can also be made from natural and herbal substitutes listed in Table II. The cavities that are extruded in both the gum and the lollipop can be made with one or more cavities that can be filled with multiple bio-enhancing and weight management substances, compiling all or some of the properties in Table II. The combination of them will achieve various results. Example: Guarana and malluang and chitosan will create energy and a feeling of "fullness" for the consumer; chromium picolinate (RE. 33, 988) and ginseng and ginger will allow the user to burn calories more efficiently).

TABLE II

| | |
|---|---|
| Siberian Ginseng | Vitamin E |
| Green Tea | Zinc |
| Casgara Sagrada | Mahuang |
| Apple Pectin | Astragalus |
| Dandelion | Guarana |
| Chickweek | Bee Pollen |
| Gymnema Sylvestre | Chromium Picolinate |
| Licorice | Bluegreen Algae |
| Bladderwrack | Royal Jelly |
| Ginger | Damiana |
| Magnesium | Lecithin |
| Sarsaparilla | Gotu Kola |
| Golden Seal | Nettles |
| Chitosan | |

The amount of all or some of these ingredients can vary, preferably being present in an amount between no less than about 0.05 mg to more than about 30 mg. The size of the gum exterior can be made of a size lest than 4.5 grams to more than 18.4 grams with the cavity center being able to accommodate a volume between 0.5 mg to more than 5 grams. The lollipop can be a total size of less than 0.65 oz. with the cavity center being a volume of no more than 0.42 oz. and no less than 4.5 grams, to a size larger then 1.35 oz. with cavity center being of at least 19 grams.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A chewing gum consisting essentially of at least one cavity that retains a liquid or semi liquid substrate wherein said liquid or semi-liquid substance consists essentially of an active ingredient consisting essentially of calcium and chromium picolinate, said active ingredient present in an amount of at least about 0.05 mg.

2. The chewing gum of claim 1 wherein said active ingredient is present in an amount of more than about 30 mg.

3. A chewing gum as set forth in claim 1, wherein said active ingredient is present in the form of a controlled release formulation.

4. A chewing gum as act forth in claim 3, wherein said controlled release formulation has desirable solubility and dissolution rates.

5. A chewing gum as set forth in claim 3, wherein said controlled release formulation comprises time release capsules.

6. A chewing gum as set forth in claim 1, wherein said active ingredient is present in an amount effective to treat osteoporosis.

7. A chewing gum as set forth in claim 1, wherein said liquid or semi-liquid substance coacts with components contained in said gum.

8. A chewing gum consisting essentially of at least one cavity that retains a liquid or semi-liquid substance wherein said liquid or semi-liquid substance consists essentially of an active ingredient consisting essentially of calcium, chromium picolinate, and magnesium, said active ingredient present in an amount of at least about 0.05 mg.

9. A chewing gum consisting essentially of at least one cavity that retains a liquid or semi-liquid substance wherein said liquid or semi-liquid substance consists essentially of an active ingredient consisting essentially of calcium, chromium picolimate, and zinc, said active ingredient present in an amount of at least about 0.05 mg.

10. A chewing gum consisting essentially of at least one cavity that retains a liquid or semi-liquid substance wherein said liquid or semi-liquid substance consists essentially of an active ingredient consisting essentially of calcium, chromium picolinate, and vitamin B, said active ingredient present in an amount of at least about 0.05 mg.

11. A chewing gum consisting essentially of at least one cavity that retains a liquid or semi-liquid substance wherein said liquid or semi-liquid substance consists essentially of an active ingredient consisting essentially of calcium, chromium picolinate and at least one component selected from the group consisting of a vitamin, a mineral supplement, guarana, ginseng, green tea, golden seal, ginger, a medicinal component, and lecithin, said active ingredient present in an amount of at least about 0.05 mg.

12. A chewing gum consisting essentially of at least one cavity that retains a liquid or semi-liquid substance wherein said liquid or semi-liquid substance consists essentially of an active ingredient consisting essentially of calcium chromium picolinate, and at least one additional component selected from the group consisting of a vitamin, a metabolic enhancer that increases a user's matabolism in order to achieve a higher caloric burn rate, a mineral supplement, guarana, ginseng, green tea, gota kola, golden seal, ginger, bee pollen, a medicinal component, nettles, and lecithin, said active ingredient present in an amount of at least about 0.05 mg.

* * * * *

UNITED STATES PATENT AND TRADEMARK OFFICE
CERTIFICATE OF CORRECTION

PATENT NO. : 6,869,614 B2
DATED : March 22, 2005
INVENTOR(S) : Barreca

It is certified that error appears in the above-identified patent and that said Letters Patent is hereby corrected as shown below:

Column 6,
Line 16, please delete the word "substrate" and insert therefor -- substance --.
Line 54, please delete "vitamin B" and insert therefor -- vitamin E --.

Column 7,
Line 1, please add a -- , -- after the word "calcium".
Line 54, please delete the word "matabolism" and insert therefor
-- metabolism --.

Signed and Sealed this

Seventh Day of June, 2005

JON W. DUDAS
*Director of the United States Patent and Trademark Office*